(12) United States Patent
Wang et al.

(10) Patent No.: US 11,738,380 B2
(45) Date of Patent: Aug. 29, 2023

(54) METHOD OF IN-SITU REMEDIATION OF ARSENIC-CONTAMINATED SOIL

(71) Applicant: Qingdao University of Technology, Qingdao (CN)

(72) Inventors: Huawei Wang, Qingdao (CN); Zijuan Lv, Qingdao (CN); Yanan Wang, Qingdao (CN); Yingjie Sun, Qingdao (CN)

(73) Assignee: Qingdao University of Technology, Qingdao (CN)

( * ) Notice: Subject to any disclaimer, the term of this patent is extended or adjusted under 35 U.S.C. 154(b) by 248 days.

(21) Appl. No.: 16/737,871

(22) Filed: Jan. 8, 2020

(65) Prior Publication Data
US 2020/0164417 A1    May 28, 2020

Related U.S. Application Data (63) Continuation-in-part of application No. PCT/CN2019/088224, filed on May 24, 2019.

(30) Foreign Application Priority Data

Nov. 28, 2018    (CN) .......................... 201811435759.7

(51) Int. Cl.
    *C12N 1/20*    (2006.01)
    *B09C 1/10*    (2006.01)
    *C12P 3/00*    (2006.01)

(52) U.S. Cl.
    CPC ................. *B09C 1/10* (2013.01); *C12N 1/20* (2013.01); *C12P 3/00* (2013.01); *B09C 2101/00* (2013.01)

(58) Field of Classification Search
    None
    See application file for complete search history.

(56) References Cited

FOREIGN PATENT DOCUMENTS

| | | |
|---|---|---|
| CN | 104140983 A | 11/2014 |
| CN | 105344709 A | 2/2016 |
| CN | 107384973 A | 11/2017 |
| CN | 107470335 A | 12/2017 |
| CN | 107916243 A | 4/2018 |
| CN | 109277404 A | 1/2019 |
| CN | 109277405 A | 1/2019 |
| CN | 109570220 A | 4/2019 |
| CN | 109570227 A | 4/2019 |
| JP | 2003112163 A | 4/2003 |

OTHER PUBLICATIONS

McCann et al. (J. of Hazardous Materials, 342 (2018) 724-731.*
Wang et al. (Environ. Pollution,258 (2020) 113482, 1-7).*
Hu et al. (Science.gov, 2014).*

* cited by examiner

*Primary Examiner* — Hope A Robinson (57) ABSTRACT

This invention relates to a method of in-situ remediation of arsenic-contaminated soil, comprising the following steps: inoculating a bacterial strain, *Pseudomonas putida* MnB1 in a culture medium where an addition amount of the bacterial strain accounts for 2-10% (v/v) of the culture medium; shaking the culture medium with the bacterial strain at a rotation speed of 100-180 rpm at 15-35° C. for 1-5 days under an aerobic condition, thereby yielding an enriched bacterial strain; and adding manganese carbonate, ammonium ferrous sulfate, sodium citrate, a yeast extract and the enriched bacterial strain to arsenic contaminated soil; adding water to the soil until the soil has a moisture content of 50-70%, stirring the soil for 5-30 minutes, and culturing the bacterial strain in the soil under an aerobic/microaerobic condition at 10-40° C. for 2-6 weeks.

4 Claims, 7 Drawing Sheets

METHOD OF IN-SITU REMEDIATION OF ARSENIC-CONTAMINATED SOIL

CROSS-REFERENCE TO RELATED APPLICATIONS

This application is a continuation-in-part of International Patent Application No. PCT/CN2019/088224 with an international filing date of May 24, 2019, designating the United States, now pending, and further claims foreign priority benefits to Chinese Patent Application No. 201811435759.7 filed Nov. 28, 2018. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND

The disclosure relates to the field of soil remediation, and more particularly to a method of in-situ remediation of arsenic-contaminated soil.

Conventional remediation technologies for arsenic contaminated soil include physical-chemical remediation, plant remediation and microbial remediation. The physical-chemical remediation technology requires bulky physical equipment and high doses of chemical materials, and may lead to secondary pollution.

The plant remediation involves the planting of the plants absorbing and accumulating heavy metals such as centipede grass. However, the plants absorbing and accumulating heavy metals in one place may not work in another place.

The microbial remediation includes biosorption technology and biological oxidation-reduction technology. The two technologies exhibit limited remediation capacity and are accompanied by the transport and conversion of arsenic.

Chinese invention patent CN107470335A discloses a method for restoring soil by utilizing a supported type biological iron-manganese bimetal oxide, which includes a treatment of phenarsonic acid pollutants in soil by it. According to the method, a carbonate ore is used as an electron donor by virtue of *Pseudomonas putida* to form a layer-like biological iron-manganese bimetal oxide on the surface of manganese carbonate, so that phenylarsonic acid type compounds and secondary products such as arsenite and arsenate in the soil can be simultaneously fixed to the surface of the ore to realize in-situ remediation or ex-situ remediation of phenylarsonic acid type contaminants. However, such method is complicated.

SUMMARY

The disclosure provides a method of in-situ remediation of arsenic-contaminated soil, and the method comprising:

1) inoculating a bacterial strain comprising *Pseudomonas putida* MnB1 in a culture medium wherein the bacterial strain accounts for 2-10% (v/v) of the culture medium; shaking the culture medium comprising the bacterial strain at a rotation speed of 100-180 rpm at 15-35° C. for 1-5 days under an aerobic condition thereby yielding an enriched bacterial strain; and 2) adding the enriched bacterial strain, manganese carbonate, ammonium ferrous sulfate, sodium citrate, and yeast extract to an arsenic contaminated soil; adding water to the soil until the soil has a moisture content of 50-70%, stirring the soil for 5-30 min, and culturing the bacterial strain in the soil under an aerobic/microaerobic condition at 10-40° C. for 2-6 weeks, so that the bacterial strain induces the formation of iron-manganese composite oxides in the soil, and transform the arsenic in the soil from an exchangeable form into a residual form.

The addition amount of the enriched bacterial strain to the soil can be 1-20 mL per 1 gram of soil; the manganese carbonate can account for 0.2-5 wt. % of the arsenic contaminated soil; the ammonium ferrous sulfate can account for 0.05-4 wt. % of the arsenic contaminated soil; the sodium citrate can account for 0.05-4 wt. % of the arsenic contaminated soil, and the yeast extract can account for 0.01-2 wt. % of the arsenic contaminated soil.

The *Pseudomonas putida* MnB1 can be originated from the American Type Culture Collection (ATCC) with an access number of 23483.

The culture medium can comprise, based on 1 liter of deionized water, 0.03-0.08 wt. % of yeast extract, 0.02-0.08 wt. % of hydrolyzed casein, 0.03-0.08 wt. % of glucose, 0.01-0.04 wt. % of calcium chloride, 0.01-0.06 wt. % of magnesium sulfate, and 0.1-0.5% (v/v) of trace elements.

The *Pseudomonas putida* MnB1 is purchased from the American Type Culture Collection (ATCC) and enriched in a culture medium, and the addition amount of the enriched bacterial strain to the soil is 1-20 mL per 1 gram of soil. With divalent iron and manganese as electron donors, the bacterial strain can induce the formation of iron-manganese composite oxides in the soil, fix the arsenic in the soil, and transform the arsenic in the soil from an exchangeable form into a residual form which exhibits poor mobility and bioavailability. The method has the advantages of convenient operation, cost-effectiveness and no secondary pollution.

DETAILED DESCRIPTION OF THE EMBODIMENTS

To further illustrate, embodiments detailing a method of in-situ remediation of arsenic-contaminated soil are described below. It should be noted that the following embodiments are intended to describe and not to limit the disclosure.

Example 1

1. Enrichment Culture of Bacterial Strain

The bacterial strain *Pseudomonas putida* MnB1 was inoculated in a culture medium, shaken and cultured at the rotation speed of 120 rpm at 30° C. for 3 days under an aerobic condition. The addition amount of the bacterial strain accounted for 2% (v/v) of the culture medium. The culture medium comprised 0.5 g of yeast extract, 0.5 g of hydrolyzed casein, 0.5 g of glucose, 0.29 g of calcium chloride, 0.5 g of magnesium sulfate, 1 mL of trace elements, and 1 liter of deionized water.

2. Soil Remediation 50 mL of the culture medium comprising the bacterial strain, 1 g of manganese carbonate, 1 g of ammonium ferrous sulfate, 0.5 g of sodium citrate, and 0.08 g of yeast extract were mixed and added to 50 g of an arsenic contaminated soil. Water was added to the soil until the soil had a moisture content of 65%. The soil was stirred for 20 min, and the bacterial strain was cultured in the soil at 30° C. for 3 weeks under an aerobic/microaerobic condition.

Figure 1:
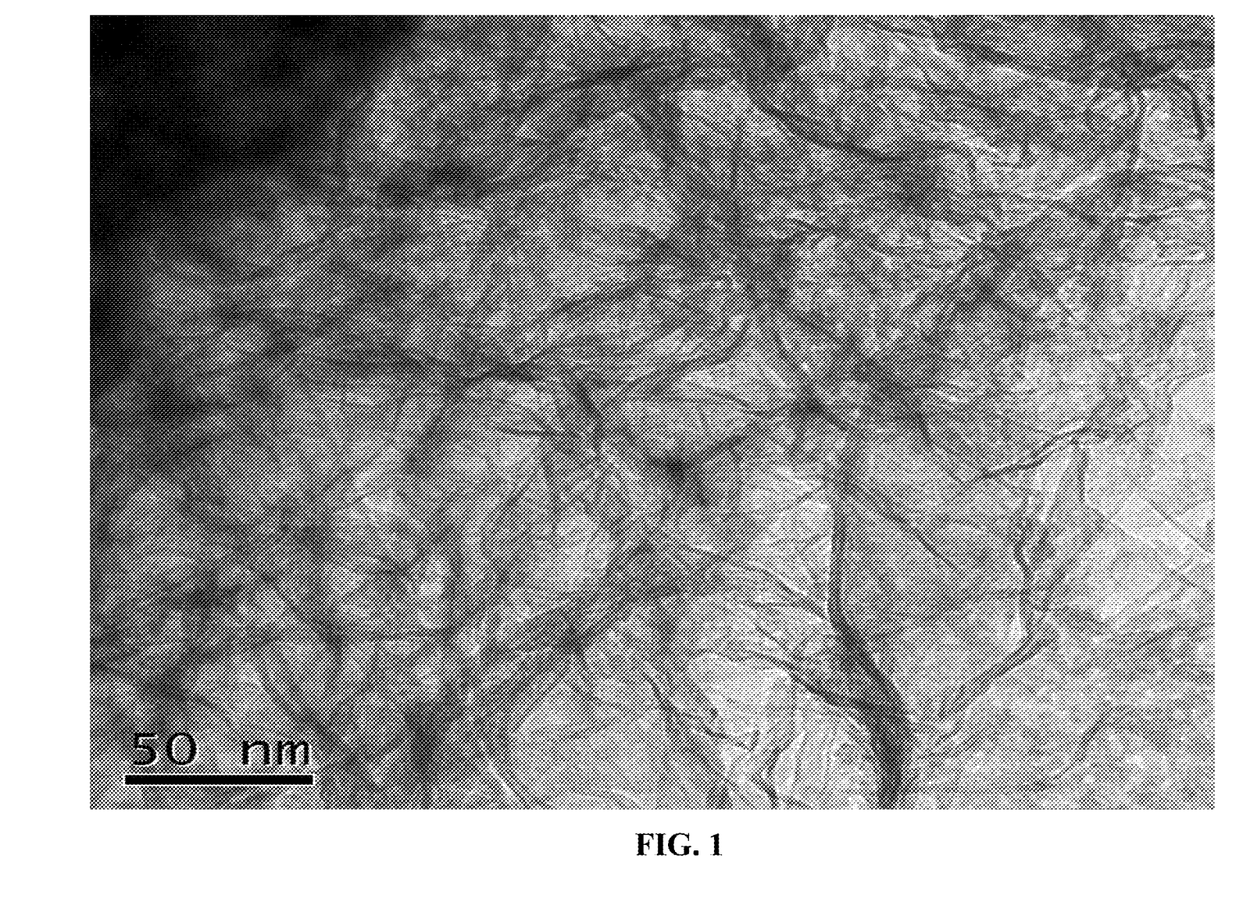
FIG. 1 is a transmission electron micrograph of in-situ induced Fe—Mn composite oxides in Example 1 of the disclosure.
Figure 2:
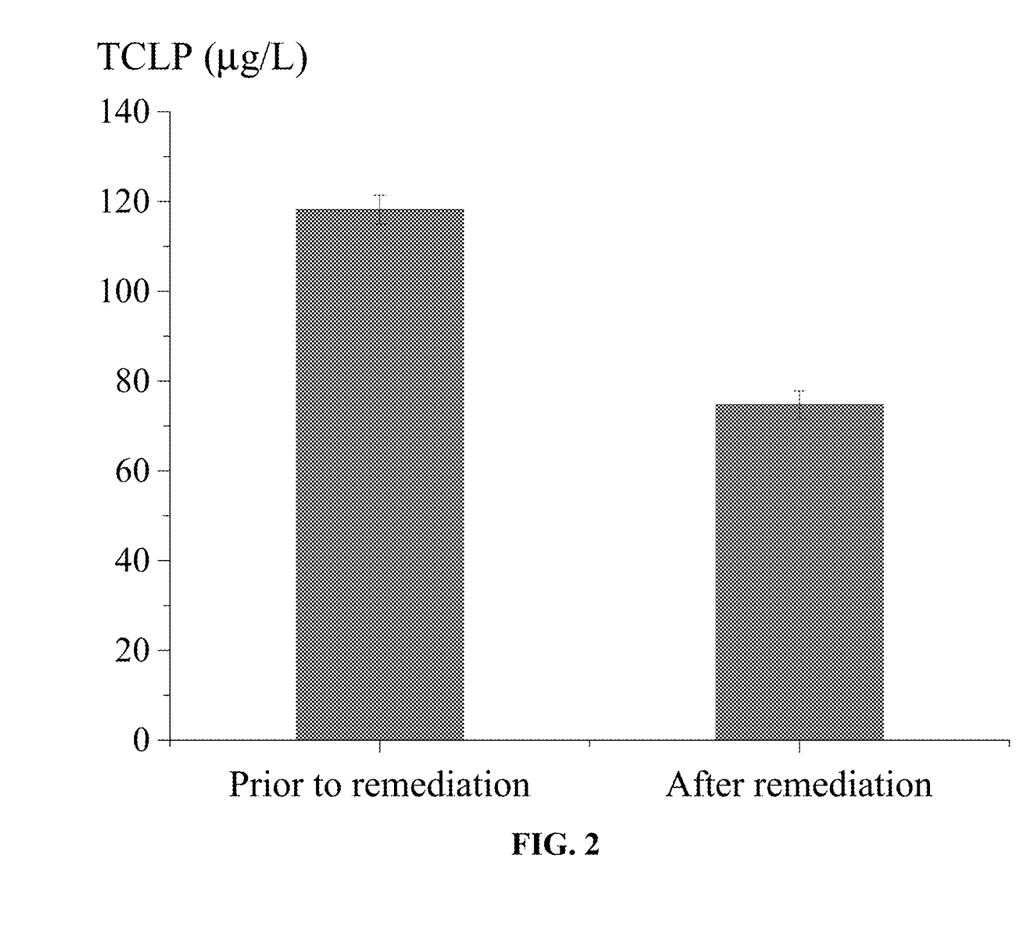
FIG. 2 shows the changes of arsenic content through toxicity characteristic leaching procedure (TCLP) prior to and after remediation in Example 1 of the disclosure.
Figure 3:
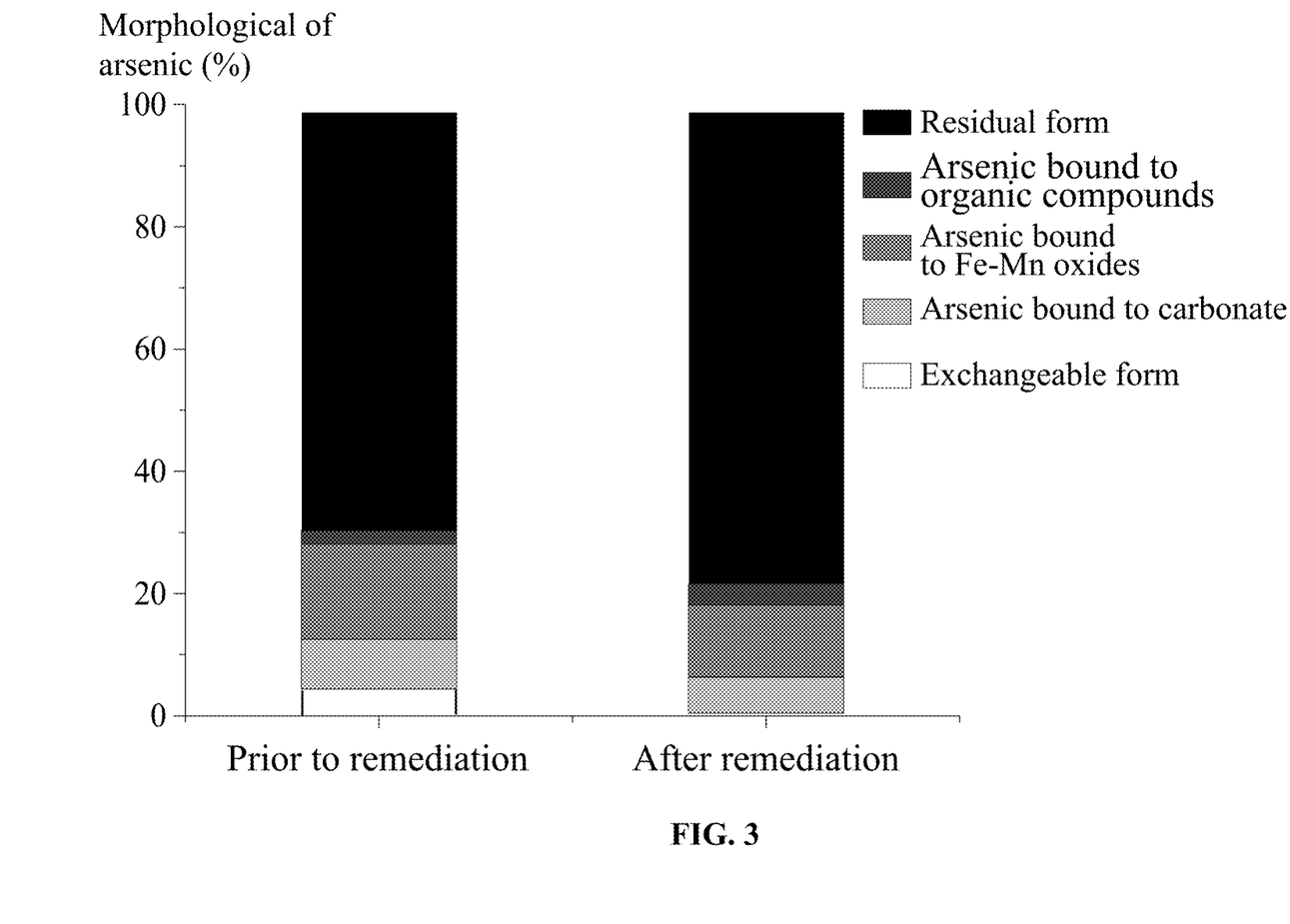
FIG. 3 shows morphological changes of arsenic prior to and after remediation in Example 1 of the disclosure.

As shown in FIG. 1, the Fe—Mn composite oxides induced by the bacterial strain were mainly amorphous Fe—Mn minerals. As shown in FIG. 2, the toxicity characteristic leaching procedure (TCLP) showed that the arsenic content was greatly reduced after the soil remediation, from 118.2 μg/L to 74.7 μg/L, with a remediation efficiency of 36.8%. FIG. 3 showed the morphological changes of arsenic prior to and after remediation, that is, the exchangeable arsenic accounted for 4.4% prior to remediation and reduced to 0.45% after remediation, and the arsenic in the residual form increased from 69.69% prior to remediation to 78.38% after remediation. The arsenic in the residual form had poor mobility and bioavailability.

Example 2

1. Enrichment Culture of Bacterial Strain

The bacterial strain *Pseudomonas putida* MnB1 was inoculated in a culture medium, shaken and cultured at the rotation speed of 150 rpm at 25° C. for 5 days under an aerobic condition. The addition amount of the bacterial strain accounted for 10% (v/v) of the culture medium. The culture medium comprised 0.8 g of yeast extract, 0.8 g of hydrolyzed casein, 0.8 g of glucose, 0.4 g of calcium chloride, 0.2 g of magnesium sulfate, 1 mL of trace elements, and 1 liter of deionized water.

2. Soil Remediation 100 mL of bacterial solution enriched of *Pseudomonas putida* MnB1, 2.5 g of manganese carbonate, 2 g of ammonium ferrous sulfate, 2 g of sodium citrate, and 0.4 g of yeast extract were mixed and added to 50 g of an arsenic contaminated soil. Water was added to the soil until the soil had a moisture content of 70%. The soil was stirred for 10 min, and the bacterial strain was cultured in the soil at 30° C. for 6 weeks under an aerobic/microaerobic condition.

Figure 4:
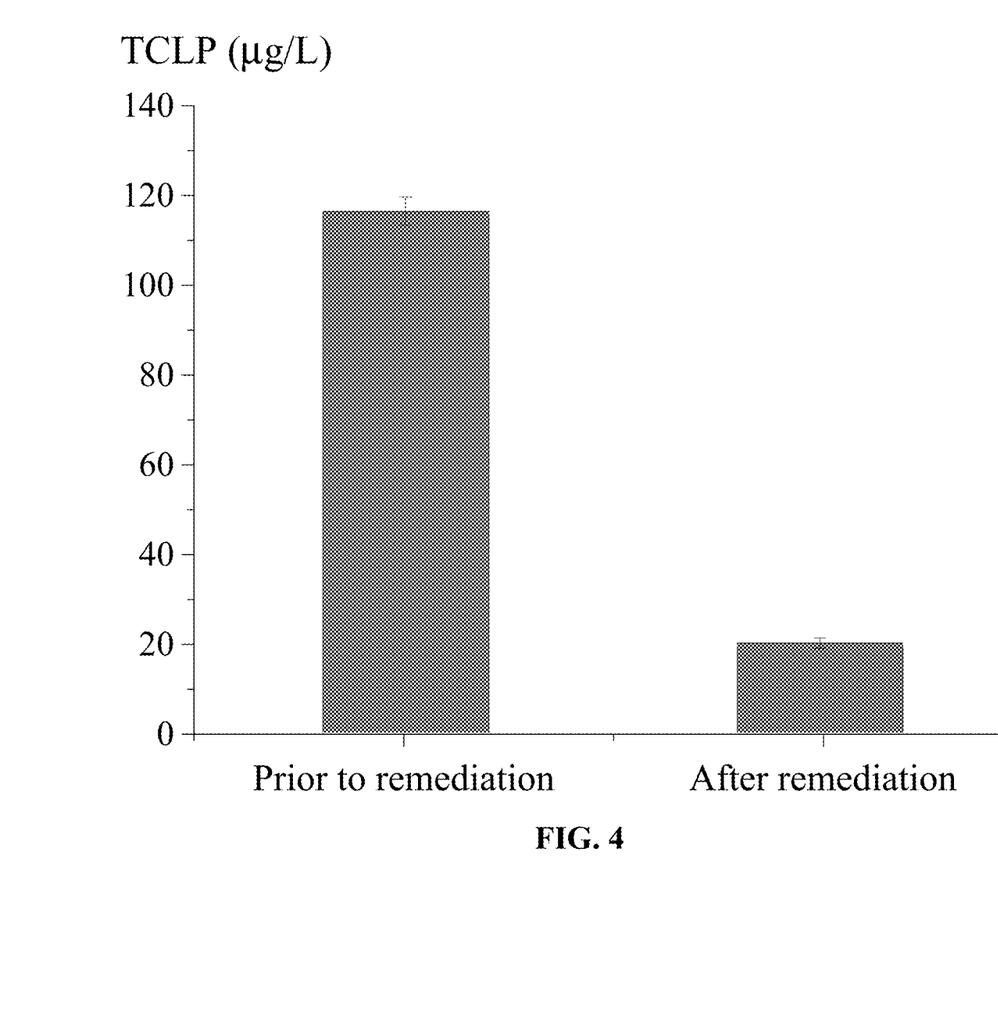
FIG. 4 shows the changes of arsenic content through toxicity characteristic leaching procedure (TCLP) prior to and after remediation in Example 2 of the disclosure.
Figure 5:
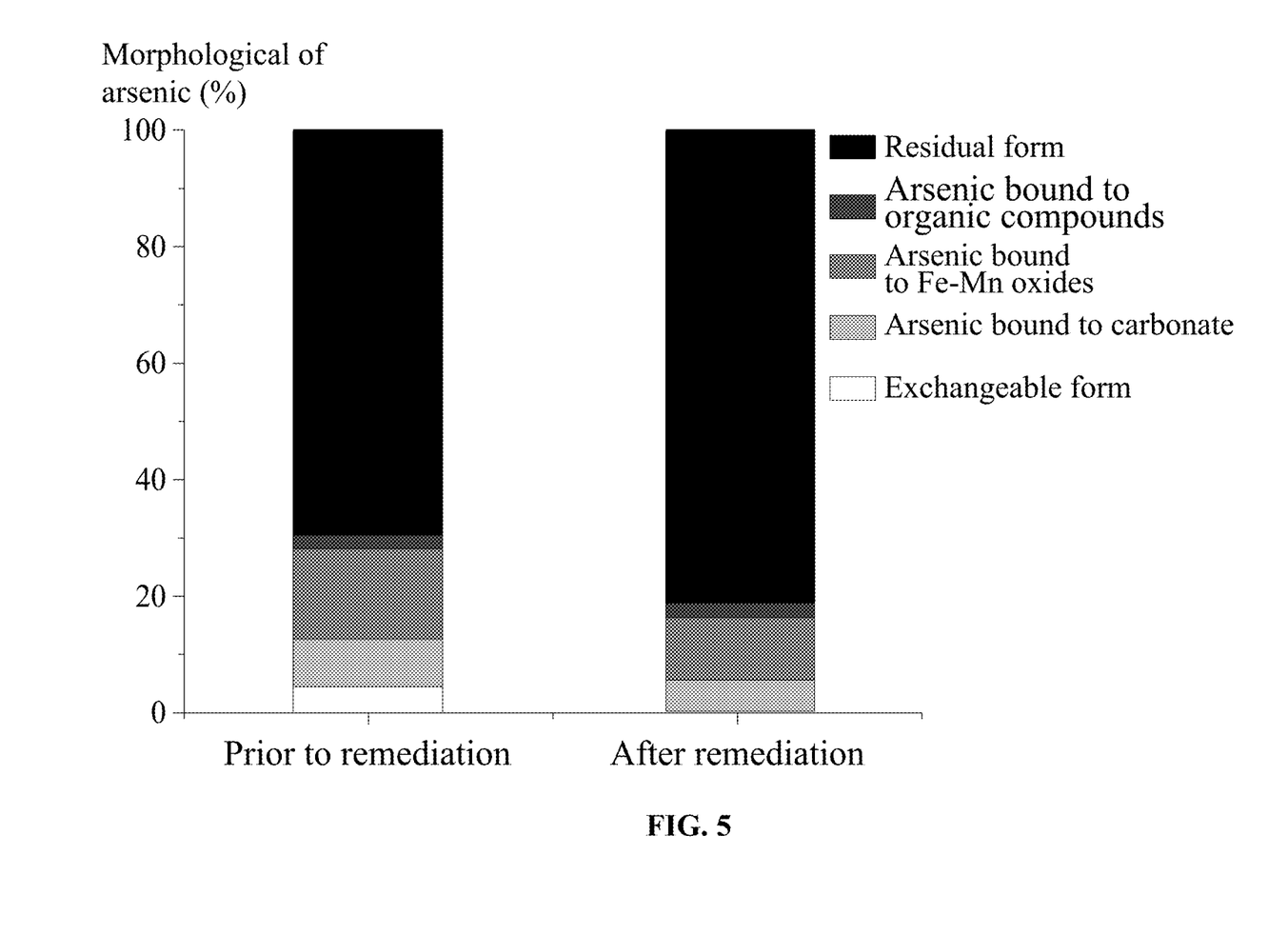
FIG. 5 shows morphological changes of arsenic prior to and after remediation in Example 2 of the disclosure.

As shown in FIG. 4, the toxicity characteristic leaching procedure (TCLP) showed that the arsenic content was greatly reduced after the soil remediation, from 118.2 μg/L to 20.2 μg/L, with a remediation efficiency of 82.9%. FIG. 5 showed the changes of arsenic fractions prior to and after remediation, that is, the exchangeable form accounted for 4.4% prior to remediation and reduced to 0.15% after remediation, and the arsenic in the residual form increased from 69.69% prior to remediation to 81.27% after remediation. The arsenic in the residual form had poor mobility and bioavailability.

Example 3

1. Enrichment Culture of Bacterial Strain

The bacterial strain *Pseudomonas putida* MnB1 was inoculated in a culture medium, shaken and cultured at the rotation speed of 150 rpm at 35° C. for 2 days under an aerobic condition. The addition amount of the bacterial strain accounted for 3% (v/v) of the culture medium. The culture medium comprised 0.45 g of yeast extract, 0.45 g of hydrolyzed casein, 0.35 g of glucose, 0.2 g of calcium chloride, 0.3 g of magnesium sulfate, 1 mL of trace elements, and 1 liter of deionized water.

2. Soil Remediation 65 mL of bacterial solution enriched of *Pseudomonas putida* MnB1, 1.5 g of manganese carbonate, 1 g of ammonium ferrous sulfate, 1.5 g of sodium citrate, and 0.34 g of yeast extract were mixed and added to 50 g of an arsenic contaminated soil. Water was added to the soil until the soil had a moisture content of 65%. The soil was stirred for 10 min, and the bacterial strain was cultured in the soil at 30° C. for 4 weeks under an aerobic/microaerobic condition.

Figure 6:
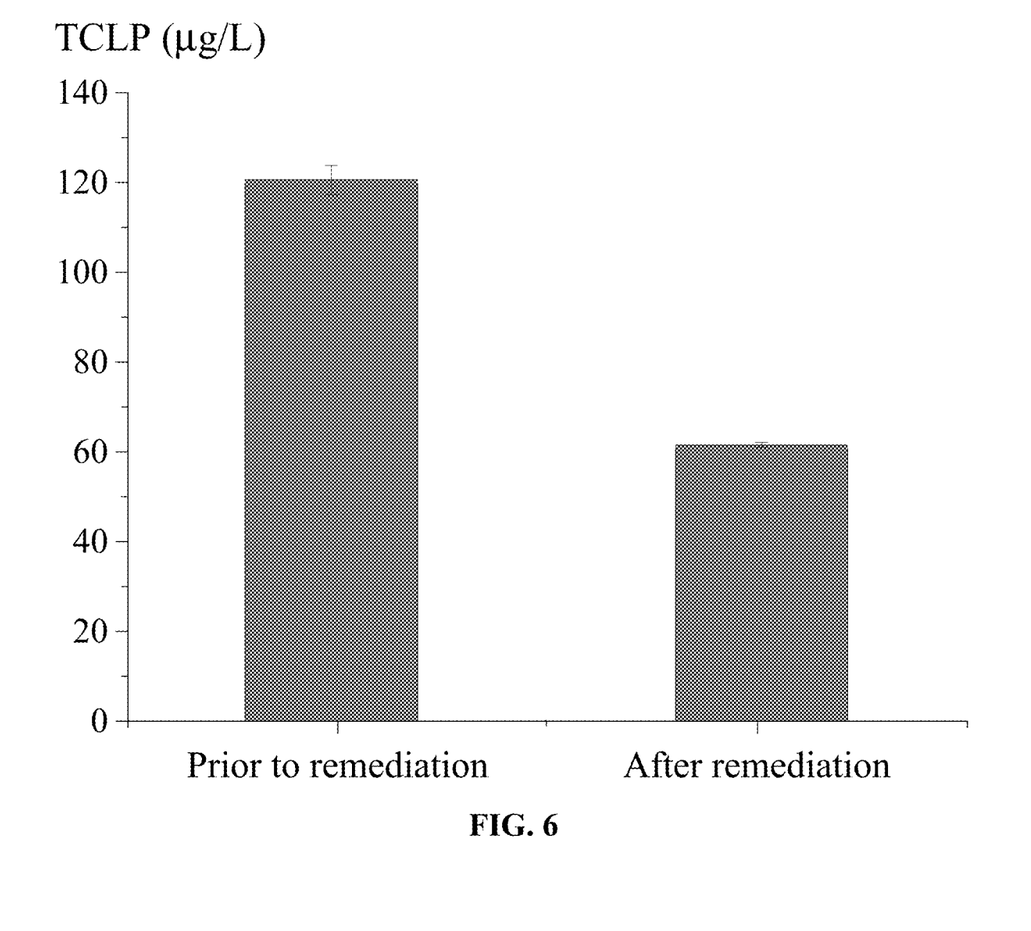
FIG. 6 shows the changes of arsenic content through toxicity characteristic leaching procedure (TCLP) prior to and after remediation in Example 3 of the disclosure.
Figure 7:
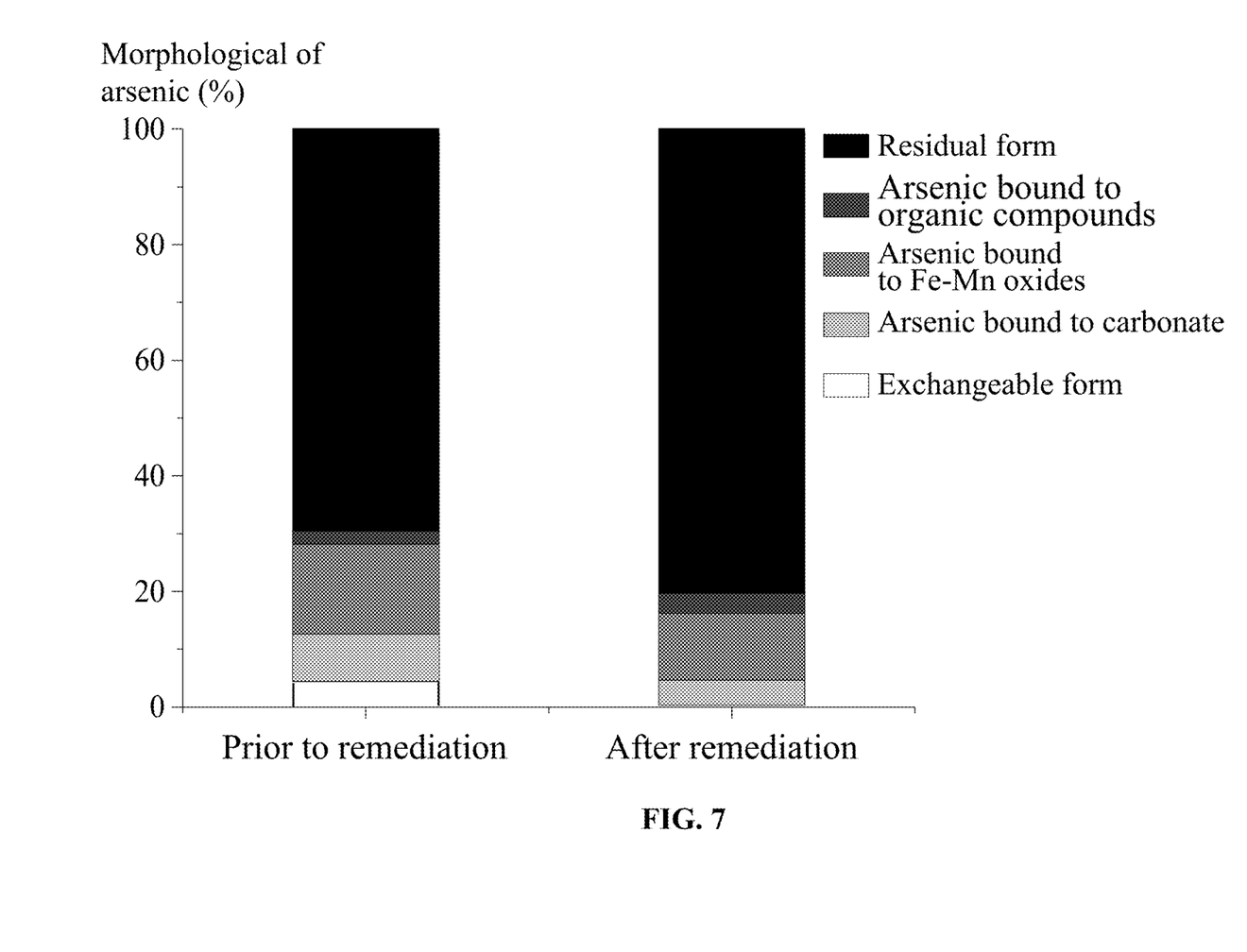
FIG. 7 shows morphological changes of arsenic prior to and after remediation in Example 3 of the disclosure.

As shown in FIG. 6, the toxicity characteristic leaching procedure (TCLP) showed that the arsenic content was greatly reduced after the soil remediation, from 118.2 μg/L to 60.2 μg/L, with a remediation efficiency of 49.1%. FIG. 7 showed the changes of arsenic fractions prior to and after remediation, that is, the exchangeable form accounted for 4.4% prior to remediation and reduced to 0.24% after remediation, and the arsenic in the residual form increased from 69.69% prior to remediation to 80.34% after remediation. The arsenic in the residual form had poor mobility and bioavailability.

The examples show that the method can remedy arsenic-contaminated soil. Under the aerobic/microaerobic conditions, the bacterial strain *Pseudomonas putida* MnB1 oxidizes the divalent iron and manganese in the culture medium to the high valence iron-manganese composite oxides. The iron-manganese composite oxides are bioactive agents for soil remediation, which can effectively reduce the exchangeable arsenic in the soil, reduce the mobility and bioavailability of arsenic in the soil, to achieve the in-situ soil remediation. The method has the advantages of convenient operation, cost-effectiveness and no secondary pollution.

It will be obvious to those skilled in the art that changes and modifications may be made, and therefore, the aim in the appended claims is to cover all such changes and modifications.

What is claimed is:

1. A method of treating arsenic contaminated soil, comprising the following steps:
   a) inoculating and culturing *Pseudomonas putida* MnB1 in a culture medium at 15-35° C. for 1-5 days under an aerobic condition, thereby producing enriched *Pseudomonas putida* MnB1,
   wherein the *Pseudomonas putida* MnB1 accounts for 2-10% (v/v) of the culture medium, and the culture medium consists essentially of 0.03-0.08 wt % of a yeast extract, 0.02-0.08 wt % of hydrolyzed casein, 0.03-0.08 wt % of glucose, 0.01-0.04 wt % of calcium chloride, 0.01-0.06 wt % of magnesium sulfate, and 0.1-0.5% (v/v) of trace elements, based on 1 liter of deionized water;

b) directly adding the enriched *Pseudomonas putida* MnB1 obtained in step a) to the arsenic contaminated soil, and adding manganese carbonate, ammonium ferrous sulfate, sodium citrate and yeast extract to the arsenic contaminated soil, wherein the enriched *Pseudomonas putida* MnB1 is added to the arsenic contaminated soil in an amount of 1-20 mL per 1 gram of the arsenic contaminated soil; and c) adding water to the arsenic contaminated soil obtained in step b) until the arsenic contaminated soil has a moisture content of 50-70%, and culturing the enriched *Pseudomonas putida* MnB1 in the arsenic contaminated soil under an aerobic or microaerobic condition at 10-40° C. for 2-6 weeks such that iron-manganese composite oxides are produced to transform arsenic in the arsenic contaminated soil from an exchangeable form into a residual form.

2. The method of claim 1, wherein the *Pseudomonas putida* MnB1 is obtained from the American Type Culture Collection (ATCC) with an access number of 23483.

3. The method of claim 1, wherein in step b), the manganese carbonate accounts for 0.2-5 wt % of the arsenic contaminated soil, the ammonium ferrous sulfate accounts for 0.05-4 wt % of the arsenic contaminated soil, and the yeast extract accounts for 0.01-2 wt % of the arsenic contaminated soil.

4. The method of claim 1, wherein the culturing *Pseudomonas putida* MnB1 in step a) is under a rotation speed of 100-180 rpm.

* * * * *